(12) United States Patent
Myntti et al.

(10) Patent No.: US 9,700,344 B2
(45) Date of Patent: Jul. 11, 2017

(54) METHOD FOR TREATING CHRONIC WOUNDS WITH AN EXTRACELLULAR POLYMERIC SUBSTANCE SOLVATING SYSTEM

(71) Applicant: Medtronic Xomed, Inc., Jacksonville, FL (US)

(72) Inventors: Matthew F. Myntti, St. Augustine, FL (US); Dana A. Oliver, Jacksonville, FL (US); James B. Hissong, Jacksonville, FL (US); Jennifer G. Medina, Jacksonville, FL (US)

(73) Assignee: MEDTRONIC XOMED, INC., Jacksonville, FL (US)

( * ) Notice: Subject to any disclaimer, the term of this patent is extended or adjusted under 35 U.S.C. 154(b) by 370 days.

(21) Appl. No.: 14/314,974

(22) Filed: Jun. 25, 2014

(65) Prior Publication Data

US 2014/0309581 A1 Oct. 16, 2014

Related U.S. Application Data (62) Division of application No. 13/124,380, filed as application No. PCT/US2009/047101 on Jun. 11, 2009, now Pat. No. 8,784,790.

(60) Provisional application No. 61/061,058, filed on Jun. 12, 2008.

(51) Int. Cl.

| A61B 17/3203 | (2006.01) |
| A61K 31/19 | (2006.01) |
| A61K 31/192 | (2006.01) |
| A61K 31/194 | (2006.01) |
| A61K 33/22 | (2006.01) |
| A61B 17/3205 | (2006.01) |
| A61K 31/198 | (2006.01) |
| A61K 45/06 | (2006.01) |
| A61K 31/09 | (2006.01) |
| A61K 31/7036 | (2006.01) |
| A61K 47/12 | (2006.01) |
| A61K 47/20 | (2006.01) |
| A61B 17/32 | (2006.01) |

(52) U.S. Cl.

CPC .......... *A61B 17/3205* (2013.01); *A61K 31/09* (2013.01); *A61K 31/19* (2013.01); *A61K 31/192* (2013.01); *A61K 31/194* (2013.01); *A61K 31/198* (2013.01); *A61K 31/7036* (2013.01); *A61K 33/22* (2013.01); *A61K 45/06* (2013.01); *A61K 47/12* (2013.01); *A61K 47/20* (2013.01); *A61B 17/3203* (2013.01); *A61B 2017/320004* (2013.01)

(58) Field of Classification Search

CPC ...... A61B 17/3203; A61B 2017/32032; A61B 5/1416; A61K 2300/00; A61K 31/19; A61K 31/192; A61K 31/194; A61K 33/22; A61K 45/06

USPC ................ 424/78.06; 514/9.4, 828
See application file for complete search history.

(56) References Cited

U.S. PATENT DOCUMENTS

| 3,422,186 A | 1/1969 | Sasmor |
| 4,002,775 A | 1/1977 | Kabara |
| 4,107,328 A | 8/1978 | Michaels |
| 4,323,551 A | 4/1982 | Parran, Jr. |
| 4,655,197 A * | 4/1987 | Atkinson ............ A61M 1/0058 601/160 |
| 4,662,829 A | 5/1987 | Nehring |
| 4,851,521 A | 7/1989 | Della Valle et al. |
| 4,902,281 A | 2/1990 | Avoy |
| 5,017,229 A | 5/1991 | Burns et al. |
| 5,145,664 A | 9/1992 | Thompson |
| 5,166,331 A | 11/1992 | Della Valle et al. |
| 5,208,257 A | 5/1993 | Kabara |
| 5,229,103 A | 7/1993 | Eagle et al. |
| 5,246,964 A | 9/1993 | Ueno |
| 5,290,552 A | 3/1994 | Sierra et al. |
| 5,326,567 A | 7/1994 | Capelli |
| 5,336,163 A | 8/1994 | DeMane et al. |
| 5,442,053 A | 8/1995 | Della Valle et al. |
| 5,480,658 A | 1/1996 | Melman |
| 5,575,815 A | 11/1996 | Slepian et al. |
| 5,601,594 A | 2/1997 | Best |
| 5,631,241 A | 5/1997 | Della Valle et al. |
| 5,644,049 A | 7/1997 | Giusti et al. |
| 5,662,913 A | 9/1997 | Capelli |

(Continued)

FOREIGN PATENT DOCUMENTS

| CN | 1174093 A | 8/2001 |
| EP | 0 530 861 B1 | 3/1993 |

(Continued)

OTHER PUBLICATIONS

Götz, Staphylococci in colonization and disease: prospective targets for drugs and vaccines; Current Opinion in Microbiology 2004, 7:477-487.*

(Continued)

*Primary Examiner* — Michael G Hartley
*Assistant Examiner* — Nabila Ebrahim
(74) *Attorney, Agent, or Firm* — Patterson Thuente Pedersen, PA (57) ABSTRACT

Chronic wounds may be treated by debriding necrotic and other devitalized tissue from the wound, and applying to the wound an extracellular polymeric substance solvating system comprising a metal ion sequestering agent, surfactant and buffering agent. The solvating system disrupts biofilms which may be present in the wound and aids or enables the resumption of normal healing.

22 Claims, 3 Drawing Sheets

(56) References Cited

U.S. PATENT DOCUMENTS

| | | | |
|---|---|---|---|
| 5,676,964 A | 10/1997 | Della Valle et al. |
| 5,693,065 A | 12/1997 | Rains, III |
| 5,709,546 A | 1/1998 | Waggoner |
| 5,716,981 A | 2/1998 | Hunter et al. |
| 5,739,176 A | 4/1998 | Dunn et al. |
| 5,763,410 A | 6/1998 | Edwardson et al. |
| 5,773,033 A | 6/1998 | Cochrum et al. |
| 5,895,781 A | 4/1999 | Neumiller et al. |
| 5,910,420 A | 6/1999 | Tuompo et al. |
| 5,925,334 A | 7/1999 | Rubin et al. |
| 5,968,542 A | 10/1999 | Tipton |
| 5,972,497 A | 10/1999 | Hirwe et al. |
| 6,001,870 A | 12/1999 | Henkel |
| 6,013,657 A | 1/2000 | Lavon et al. |
| 6,063,061 A | 5/2000 | Wallace et al. |
| 6,071,305 A | 6/2000 | Brown et al. |
| 6,129,761 A | 10/2000 | Hubbell |
| 6,143,330 A | 11/2000 | Aaltonen et al. |
| 6,156,294 A | 12/2000 | Mautone |
| 6,156,792 A | 12/2000 | Hatton et al. |
| 6,200,587 B1 | 3/2001 | Soe et al. |
| 6,203,822 B1 | 3/2001 | Schlesinger et al. |
| 6,224,857 B1 | 5/2001 | Romeo et al. |
| 6,248,371 B1 | 6/2001 | Domenico |
| 6,284,804 B1 | 9/2001 | Singh et al. |
| 6,312,725 B1 | 11/2001 | Wallace et al. |
| 6,342,251 B1 | 1/2002 | Illum et al. |
| 6,372,229 B1 | 4/2002 | Ollerenshaw et al. |
| 6,375,963 B1 | 4/2002 | Repka et al. |
| 6,395,295 B1 | 5/2002 | Hills et al. |
| 6,395,746 B1 | 5/2002 | Cagle et al. |
| 6,423,333 B1 | 7/2002 | Stedronsky et al. |
| 6,423,694 B1 | 7/2002 | Drutz et al. |
| 6,533,749 B1 | 3/2003 | Mitusina et al. |
| 6,541,116 B2 | 4/2003 | Michal et al. |
| 6,541,460 B2 | 4/2003 | Petito |
| D478,984 S | 8/2003 | Hall et al. |
| 6,610,314 B2 | 8/2003 | Koenig et al. |
| 6,613,084 B2 | 9/2003 | Yang |
| 6,616,913 B1 | 9/2003 | Mautone |
| 6,623,513 B2 | 9/2003 | Biel |
| 6,623,521 B2 | 9/2003 | Steinke et al. |
| 6,632,457 B1 | 10/2003 | Sawhney |
| 6,676,930 B2 | 1/2004 | Mautone |
| 6,685,697 B1 | 2/2004 | Arenberg et al. |
| 6,686,346 B2 | 2/2004 | Nilsson et al. |
| 6,706,290 B1 | 3/2004 | Kajander et al. |
| 6,723,709 B1 | 4/2004 | Pressato et al. |
| 6,762,160 B2 | 7/2004 | Barbeau et al. |
| 6,770,729 B2 | 8/2004 | Van Antwerp |
| 6,812,196 B2 | 11/2004 | Rees et al. |
| 6,855,678 B2 | 2/2005 | Whiteley |
| 6,867,233 B2 | 3/2005 | Roselle et al. |
| 6,869,938 B1 | 3/2005 | Schwartz et al. |
| 6,891,037 B1 | 5/2005 | Hasler et al. |
| 6,919,348 B2 | 7/2005 | Wei |
| 6,936,579 B2 | 8/2005 | Urban |
| 6,953,772 B2 | 10/2005 | Lopes |
| 6,962,813 B2 | 11/2005 | Pier et al. |
| 6,989,195 B2 | 1/2006 | Anderson |
| 7,090,882 B2 | 8/2006 | Koeford et al. |
| 7,119,217 B2 | 10/2006 | Jiang et al. |
| 7,128,897 B2 * | 10/2006 | Osbakken ............ A61K 9/0043 424/434 |
| 7,220,431 B2 | 5/2007 | Sawchuk et al. |
| 7,238,363 B2 | 7/2007 | Mansouri et al. |
| 7,244,841 B2 | 7/2007 | Love et al. |
| 7,341,983 B2 | 3/2008 | Pedersen et al. |
| 7,410,480 B2 | 8/2008 | Muni et al. |
| 7,446,089 B2 | 11/2008 | Singh et al. |
| 7,494,963 B2 | 2/2009 | Ahmed et al. |
| 7,544,192 B2 | 6/2009 | Eaton et al. |
| 7,714,011 B2 | 5/2010 | Clarot et al. |
| 7,727,547 B2 | 6/2010 | Fortune |
| 7,959,943 B2 | 6/2011 | Hissong et al. |
| 7,976,875 B2 | 7/2011 | Myntti |
| 8,044,156 B2 | 10/2011 | Tamareselvy et al. |
| 8,062,246 B2 | 11/2011 | Moutafis et al. |
| 8,476,319 B2 | 7/2013 | Scholz et al. |
| 2001/0018460 A1 | 8/2001 | Doi et al. |
| 2001/0044651 A1 | 11/2001 | Steinke et al. |
| 2001/0051613 A1 | 12/2001 | Illum et al. |
| 2002/0022588 A1 | 2/2002 | Wilkie et al. |
| 2002/0029015 A1 | 3/2002 | Camenzind et al. |
| 2002/0055158 A1 | 5/2002 | Greene et al. |
| 2002/0187918 A1 | 12/2002 | Urban |
| 2003/0009213 A1 | 1/2003 | Yang |
| 2003/0062147 A1 | 4/2003 | Schoen et al. |
| 2003/0079758 A1 | 5/2003 | Siegel et al. |
| 2003/0083219 A1 | 5/2003 | Rees et al. |
| 2003/0133883 A1 | 7/2003 | Finnegan et al. |
| 2003/0139382 A1 | 7/2003 | Wall et al. |
| 2003/0157687 A1 | 8/2003 | Greene et al. |
| 2003/0199969 A1 | 10/2003 | Steinke et al. |
| 2003/0235602 A1 | 12/2003 | Schwartz |
| 2004/0101506 A1 | 5/2004 | Fust |
| 2004/0106987 A1 | 6/2004 | Palasis et al. |
| 2004/0110738 A1 | 6/2004 | Gillis et al. |
| 2004/0116958 A1 | 6/2004 | Gopferich et al. |
| 2004/0117006 A1 | 6/2004 | Lewis et al. |
| 2004/0143001 A1 | 7/2004 | Love et al. |
| 2004/0204399 A1 | 10/2004 | Oshbakken et al. |
| 2004/0213758 A1 | 10/2004 | Sefton et al. |
| 2004/0214753 A1 | 10/2004 | Britten et al. |
| 2005/0003007 A1 | 1/2005 | Boix et al. |
| 2005/0032668 A1 | 2/2005 | Pedersen et al. |
| 2005/0042240 A1 | 2/2005 | Utterberg et al. |
| 2005/0043706 A1 | 2/2005 | Eaton et al. |
| 2005/0064508 A1 | 3/2005 | Belcher et al. |
| 2005/0080396 A1 | 4/2005 | Rontal |
| 2005/0106728 A1 | 5/2005 | Burgess et al. |
| 2005/0147679 A1 | 7/2005 | Petito et al. |
| 2005/0220895 A1 | 10/2005 | Bucalo et al. |
| 2005/0226937 A1 | 10/2005 | O'Hagan et al. |
| 2005/0244339 A1 | 11/2005 | Jauering et al. |
| 2005/0282722 A1 | 12/2005 | McReynolds et al. |
| 2006/0003008 A1 | 1/2006 | Gibson et al. |
| 2006/0018945 A1 * | 1/2006 | Britigan ............... A01N 59/16 424/423 |
| 2006/0035808 A1 | 2/2006 | Ahmed et al. |
| 2006/0045850 A1 | 3/2006 | Namburi et al. |
| 2006/0051385 A1 | 3/2006 | Scholz |
| 2006/0106361 A1 | 5/2006 | Muni et al. |
| 2006/0205621 A1 | 9/2006 | Borazjani et al. |
| 2006/0210605 A1 | 9/2006 | Chang et al. |
| 2007/0207192 A1 | 9/2007 | Holl et al. |
| 2007/0264226 A1 | 11/2007 | Karagoezian et al. |
| 2007/0264296 A1 * | 11/2007 | Myntti ................. A01N 25/30 424/405 |
| 2007/0264310 A1 | 11/2007 | Hissong et al. |
| 2007/0264342 A1 | 11/2007 | Oliver et al. |
| 2007/0264353 A1 | 11/2007 | Myntti et al. |
| 2008/0010947 A1 | 1/2008 | Huang et al. |
| 2008/0248558 A1 | 10/2008 | Deinhammer et al. |
| 2009/0005339 A1 | 1/2009 | Scholz et al. |
| 2010/0240770 A1 | 9/2010 | Qi et al. |

FOREIGN PATENT DOCUMENTS

| | | |
|---|---|---|
| EP | 1 374 856 A1 | 1/2004 |
| FR | 2 710 529 A1 | 4/1995 |
| JP | 52-007428 | 1/1977 |
| JP | H11130602 A | 5/1999 |
| JP | HEI 11-130608 | 5/1999 |
| JP | 2003-221328 | 8/2003 |
| RU | 2 125 432 C1 | 1/1999 |
| RU | 222 8203 | 5/2004 |
| SU | 1128917 A1 | 12/1984 |
| SU | 1699430 A1 | 12/1991 |
| WO | WO 91/19503 | 12/1991 |
| WO | WO 92/16245 | 10/1992 |
| WO | WO 93/18747 | 3/1993 |
| WO | WO 94/05330 | 3/1994 |
| WO | WO 95/03036 | 2/1995 |

(56) References Cited

FOREIGN PATENT DOCUMENTS

| WO | WO 97/38698 | | 10/1997 | |
|---|---|---|---|---|
| WO | WO 98/09622 | | 3/1998 | |
| WO | WO 99/27905 | A | 6/1999 | |
| WO | WO 9955368 | A1 * | 11/1999 | ............ C07K 14/21 |
| WO | WO 00/21510 | | 4/2000 | |
| WO | WO 00/56283 | | 9/2000 | |
| WO | WO 00/69348 | A1 | 11/2000 | |
| WO | WO 03/061579 | A2 | 7/2003 | |
| WO | WO 03/092745 | A1 | 11/2003 | |
| WO | WO 2004/009143 | A1 | 1/2004 | |
| WO | WO 2004/024187 | A2 | 3/2004 | |
| WO | WO 2005/000029 | A2 | 1/2005 | |
| WO | WO 2005/030297 | A1 | 4/2005 | |
| WO | WO 2005/089670 | A1 | 9/2005 | |
| WO | WO 2006/099386 | A2 | 9/2006 | |
| WO | WO 2007/074454 | A2 | 7/2007 | |
| WO | WO 2007/100382 | A2 | 9/2007 | |
| WO | WO 2007/134055 | A1 | 11/2007 | |
| WO | WO 2007/136558 | A2 | 11/2007 | |
| WO | WO 2008/097317 | A1 | 8/2008 | |
| WO | WO 01/22907 | A1 | 4/2011 | |

OTHER PUBLICATIONS

Pluronic® P65, Block Copolymer Surfactant Technical Bulletin, BASF Corporation, 1 page (2004).
Chamberlain, N.R. Ph.D., The Microbiology of Wounds, Department of Microbiology/Immunology KCOM, 102nd Missouri Osteopathic Annual Convention, 31 pages (May 6, 2000).
Polyhexamethylene Biguanide (PHMB), Product Stewardship Summary, Arch®, 7 pages (Apr. 2008).
Pulsavac® Wound Debridement System, Product Information Brochure, Zimmer, 5 pages (1998).
Sholar, A. M.D. et al., Wound Healing, Chronic Wounds, 11 pages (May 23, 2003).
Guidance on the use of debriding agents and specialist wound care clinics for difficult to heal surgical wounds, National Institute for Clinical Excellence, Technology Appraisal Guidance, No. 24, 14 pages (Apr. 2001).
Cunningham et al., Are all chronic wounds essentially the same?, Module 7, Section 5: Biofilms in Chronic Wounds, from Biofilms: The Hypertextbook, 2 pages (Oct. 27, 2006), downloaded from www.coe.montana.edu/biofilmbook/MODULE_07/Mod07_S05_Blue.htm.
V.A.C.® Instill™, Dual Therapies. One Advanced Wound Healing System., KCI®, Product Information Brochure, 6 pages (2005).
James, G.A. Ph.D., et al., Biofilms in chronic wounds, Wound Rep. Reg., 16:37-44 (2008).
Costerton, J.W. et al., Bacterial Biofilms: A Common Cause of Persistent Infections, Science, vol. 284:1318-1322 (May 21, 1999).
Parsek, M.R. et al., Bacterial Biofilms: An Emerging Link to Disease Pathogenesis, Annual Review of Microbiology, 57:677-701 (2003).
Donlan, R.M. et al., Reviews, Clinical Microbiology Reviews, vol. 15, No. 2, pp. 167-193 (Apr. 2002).
The Queen Elizabeth Hospital Research Day 2007, Programme & Abstracts, Main Lecture Theatre, Government of South Australia, 8 pages (Oct. 19, 2007).
Post, J.C., "Direct evidence of bacterial biofilms in otitis media", Laryngoscope 111(12):2083-94 (2001).
Ehrlich et al., "Mucosal Biofilm Formation on Middle-Ear Mucosa in the Chinchilla Model of Otitis Media", JAMA 287(13):1710-15 (2002).
Fergie, N. et al., "Is otitis media with effusion a biofilm infection?", Clin Otolaryngol Allied Sci. 29(1):38-46 (2004).
Ferguson B.J. and Stolz D.B., "Demonstration of biofilm in human bacterial chronic rhinosinusitis", Am J Rhinol 19:452-457, (2005).
Ramadan H.H., Sanclement J.A. and Thomas J.G., "Chronic rhinosinusitis and biofilms", Otolaryngol Head Neck Surg. 132:414-417,(2005).

Benninger M.S., Ferguson B.J., Hadley J.A., et al., "Adult chronic rhinosinusitis: Definitions, diagnosis, epidemiology, and pathophysiology", Otolaryngol Head Neck Surg 129 (3 suppl):S1-S32, (2003).
Nadel D.M., Lanza D.C., and Kennedy D.W., "Endoscopically guided cultures in chronic sinusitis", Am J Rhinol 12:233-241, (1998).
Stepanovic S, Vukovic D, Dakic I, et al., "A modified microtiterplate test for quantification of staphylococcal biofilm formation", J Microbiol Methods 40:175-179, (2000).
Gotz F., "*Staphylococcus* and biofilms", Mol Microbiol 43:1367-1378, (2002).
Lethbridge-Ç ejku M, Rose D, Vickerie J. Summary health statistics for US adults: National Health Interview Survey, 2004. National Center for Health Statistics. Vital Health Stat 2006; 10 (228). Available: http://www.cdc.gov/nchs/fastats/sinuses.htm.
Rosiak, J.M. et al., "Radiation Formation of Hydrogels for Biomedical Purposes. Some Remarks and Comments", Radiat. Phys. Chem. vol. 46, No. 2, pp. 161-168, (1995).
Costerton J.W., Stewart P.S. and Greenberg E.P., "Bacterial biofilms: A common cause of persistent infections", Science 284:1318-1322, (1999).
Morris D.P. and Hagr A., "Biofilm: Why the sudden interest?" J Otolaryngol 34(suppl 2):S56-S5, (2005).
Hall-Stoodley L, Hu F.Z., Gieseke A, et al., "Direct detection of bacterial biofilms on the middle-ear mucosa of children with chronic otitis media." JAMA 296:202-211, (2006).
Sanderson A.R., Leid J.G., and Hunsaker D., "Bacterial biofilms on the sinus mucosa of human subjects with chronic rhinosinusitis", Laryngoscope 116:1121-1126 (2006).
Sanclement J.A., Webster P., Thomas J., and Ramadan H.H., "Bacterial biofilms in surgical specimens of patients with chronic rhinosinusitis", Laryngoscope 115:578-582, (2005).
Bendouah Z., Barbeau J., Hamad W.A., and Desrosiers M., "Biofilm formation by *Staphylococcus aureus* and Pseudomonas aeruginosa is associated with an unfavorable evolution after surgery for chronic sinusitis and nasal polyposis", Otolaryngol Head Neck Surg. 134:991-996, (2006).
Bhattacharyya N., and Kepnes L.J., "The microbiology of recurrent rhinosinusitis after endoscopic sinus surgery", Arch Otolaryngol Head Neck Surg. 125:1117-1120, (1999).
Cryer J., Schipor I., Perloff J.R., and Palmer J.N., "Evidence of bacterial biofilms in human chronic sinusitis", ORL J Otorhinolaryngol Relat Spec 66:155-158, (2004).
Meltzer E.O., Hamilos D.L., Hadley J.A., et al., "Rhinosinusitis: Establishing definitions for clinical research and patient care", J Allergy Clin Immunol 114(suppl):S155-S212, (2004).
Chiu A.G., and Kennedy D.W., "Surgical management of chronic rhinosinusitis and nasal polyposis: a review of the evidence", Curr Allergy Asthma Rep 4:486-489, (2004).
Bhattacharyya N., "Clinical outcomes after endoscopic sinus surgery", Curr Opin Allergy Clin Immunol 6:167-171, (2006).
Wormald P.J., Psaltis A., and Ha K., "A sheep model for the study of biofilms in sinusitis", In Programs and abstracts of the 52nd Annual Meeting of the American Rhinologic Society, Toronto, Ontario, Canada, Sep. 16, 2006.
Anglen J.O., Apostoles S., Christensen G., and Gainor B., "The efficacy of various irrigation solutions in removing slime-producing *Staphylococcus*", J Orthop Trauma 8:390-396, (1994).
Chole, Richard A. and Faddis, Brian T., Evidence for Microbial Biofilms in Cholesteatomas, Arch Otolaryngol Head and Neck Surg.; 128: 1129-1133 (2002) Downloaded Apr. 17, 2007 from Medtronic Xomed at www.archoto.com.
Desrosiers M. Refractory chronic rhinosinusitis: pathophysiology and management of chronic rhinosinusitis persisting after endoscopic sinus surgery. Curr Allergy Asthma Rep;4:200-7 (2004).
Smith TL, Batra PS, Seiden AM, Hannley M. Evidence supporting endoscopic sinus surgery in the management of adult chronic sinusitis: a systematic review. Am J Rhinol;19:537-43 (2005).
Perloff JR, Palmer JN. Evidence of bacterial biofilms on frontal recess stents in patients with chronic rhinosinusitis. Am J Rhinol;18:377-80 (2004).

(56) References Cited

OTHER PUBLICATIONS

Wright ED, Frenkiel S. Infectious adult rhinosinusitis: etiology, diagnosis, and management principles. J Otolaryngol;34(suppl 1):S7-13 (2005).
Luong A, Marple BF. Sinus surgery: indications and techniques. Clin Rev Allergy Immunol;30:217-22 (2006).
Abdi-Ali A, Mohammadi-Mehr M, Agha Alaei Y. Bactericidal activity of various antibiotics against biofilm-producing Pseudomonas aeruginosa. Int J Antimicrob Agents 2206;27:196-200.
Jefferson KK, Goldmann DA, Pier GB. Use of confocal microscopy to analyze the rate of vancomycin penetration through *Staphylococcus aureus* biofilms. Antimicrob Agents Chemother; 49:2467-73 (2005).
Walters MC 3rd, Roe F, Bugnicourt A, Franklin MJ, Stewart PS. Contributions of antibiotic penetration, oxygen limitation, and low metabolic activity to tolerance of Pseudomonas aeruginosa biofilms to ciprofloxacin and tobramycin. Antimicrob Agents Chemother;47:317-23 (2003).
Palmer JN. Bacterial biofilms: do they play a role in chronic sinusitis? Otolaryngol Clin N Am;38:1193-1201 (2005).
Donlan RM. Biofilms: microbial life on surfaces. Emerg Infect Dis;8:881-90 (2002).
Potera C. Forging a link between biofilms and disease. Science; 283:1837, 1839 (1999).
Post JC, Stoodley P, Hall-Stoodley L, Ehrlich GD. The role of biofilms in otolaryngologic infections. Curr Opin Otolaryngol Head Neck Surg;12:185-90 (2004).
Tonnaer EL, Graamans K, Sanders EA, Curfs JH. Advances in understanding the pathogenesis of pneumococcal otitis media. Pediatr Infect Dis J;25:546-52 (2006).
Rayner MG, Zhang Y, Gorry MC, Chen Y, Post CJ, Ehrlich GD. Evidence of bacterial metabolic activity in culture-negative otitis media with effusion. JAMA;279:296-9 (1998).
Dingman JR, Rayner MG, Mishra S, Zhang Y, Ehrlich MD, Post JC, et al. Correlation between presence of viable bacteria and presence of endotoxin in middle-ear effusions. J Clin Microbiol;36:3417-9 (1998).
Perloff JR, Palmer JN. Evidence of bacterial biofilms in a rabbit model of sinusitis. Am J Rhinol;19:1-9 (2005).
Chiu A, Antunes M, Feldman M, Cohen N. Dose-dependent effects of topical tobramycin in an animal model of Pseudomonas sinusitis. In: Programs and abstracts of the 52nd Annual Meeting of the American Rhinologic Society; Sep. 16, Toronto, ON, Canada (2006).
Witterick IJ, Kolenda J. Surgical management of chronic rhinosinusitis. Immunol Allergy Clin N Am;24:119-34 (2004).
Lieu JE, Piccirillo JF. Methodologic assessment of studies on endoscopic sinus surgery. Arch Otolaryngol Head Neck Surg;129:1230-5 (2003).
Lavigne F, Tulic MK, Gagnon J, Hamid Q. Selective irrigation of the sinuses in the management of chronic rhinosinusitis refractory to medical therapy: a promising start. J Otolaryngol 2004;33:10-16.
Yamada et al., "Chitosan Based Water-Resistant Adhesive. Analogy to Mussel Glue", *Biomacromolecules 2000*, 1 (2), pp. 252-258 (Apr. 13, 2000).
"Protein Polymer Technologies Product Research" dated Mar. 28, 2006, 2 pages, downloaded from the Internet Archive at: http://web.archive.org/web/20060328113942/www.ppti.com/Market/Research.html.
Gross, Charles W., et al., "Autologus Fibrin Sealant Reduces Pain After Tonsillectomy", The Laryngoscope 111, pp. 259-263 (Feb. 2001).
Kitajiri et al., "Relief of Post-Tonsillectomy Pain by Release of Lidocaine From Fibrin Glue", The Laryngoscope 111, pp. 642-644 (Apr. 2001).
Vaiman Michael et al., "Fibrin Sealant Reduces Pain After Tonsillectomy: Prospective Randomized Study", Annals of Otology, Rhinology & Laryngology 115 (7), pp. 483-489 (2006).

Archer, Sanford M. MD, *Nasal Polyps, Nonsurgical Treatment*, eMedicine, dated Oct. 19, 2004, downloaded from the Internet Archive at: http://web.archive.org/web/20041019082359/http://www.emedicine.com/ent/topic334.htm.
Atridox®, Package insert and Carton Label Rev 7 (Feb. 2003).
Kumar et al., "Inhibition of Inflammation and Roflumilast and Dexamethasone in Murine Chronic Asthma", Journal of Pharmacology and Experimental Therapeutics, vol. 307, No. 1, pp. 349-355 (2003).
CollaGenex Atridox® web page, dated Sep. 26, 2004, downloaded from the Internet Archive at: http://web.archive.org/web/20041205004132/collagenex.com/pr_atridox.asp.
Lechapt-Zalcman et al., *Increased expression of matrix metalloproteinase-9 in nasal polyps*, Journal of Pathology, 193:233-241 (2001).
Kyung, Lee S. et al., *Doxycycline reduces airway inflammation and hyperresponsiveness in a murine model of toluene diisocyanate-induced asthma*, Journal of Allergy and Clinical Immunology [online] (May 2004).
Watelet, J.B. et al., *Matrix metalloproteinases MMP-7, MMP-9 and their tissue inhibitor TIMP-1: expression in chronic sinusitis vs. nasal polyposis*, Allergy, 59:54-60 (2004).
Plateltex, "Reduce fibrosis-Reducing scarring-Autologous Plateletts", accessed on Jan. 26, 2010 from: http://www.plateltex.com/lp_reduce_fibrosis.html.
Stoeckli, Sandro J. et al., "A Prospective Randomized Double-Blind Trial of Fibrin Glue for Pain and Bleeding After Tonsillectomy", Laryngoscope 109: pp. 652-655, (Apr. 1999).
Granick Mark MD et al., "Toward a common language: surgical wound bed preparation and debridement", Wound Repair and Regeneration, 14, S1-S10, © the Wound Healing Society, (2006).
Stetter, Christopher et al., "Skin grafting of a chronic leg ulcer with combined Versajet™—V.A.C. therapy", XP-002566870 Case Reports, JDDG, 4:739-742 (2006).
Nagoba, B.S. et al., A Simple and Effective Approach for the Treatment of Chronic Wound Infections Caused by Multiple Antibiotic Resistant *Escherichia coli*, Journal of Hospital Infection, 69:177-180 (2008).
Banin, Ehud et al., "Chelator-Induced Dispersal and Killing of *Pseudomonas aeruginosa* Cells in a Biofilm", Applied and Environmental Microbiology, vol. 72, No. 3, pp. 2064-2069 (Mar. 2006).
Chang, D.M., The Binding of Free Calcium Ions in Aqueous Solution Using Chelating Agents, Phosphates and Poly (Acrylic Acid), JAOCS, vol. 60, No. 3, pp. 618-622 (Mar. 1983).
"Medicine Encyclopedia" M., RLS, Miramistin solution 0.01%, p. 561 ( 2001).
Ambrose et al., In Vitro Studies of Water Activity and Bacterial Growth Inhibition of Sucrose-Polyethylene Glycol 400-Hydrogen Peroxide and Xylose-Polyethylene Glycol 400-Hydrogen Peroxide and Xylose-Polyethylene Glycol 400-Hydrogen Peroxide Pastes Used to Treat Infected Wounds, Antimicrob Agents Chermo, vol. 35, No. 9, pp. 1799-1803 (Sep. 1991).
*Stedman's Medical Dictionary*, 24th Edition, pp. 1292-1294 (1983).
Phillips, P. et al., "Bacterial Biofilms in wounds", Wound Healing Southern Africa, vol. 1, No. 2, pp. 10-12 (2008).
Pitten et al., "*Efficacy of Cetylpyridinium Chloride Used as Oropharyngeal Antiseptic*", Arzneimittelforschung/Drug Research 51, 7 pp. 588-595 (Jul. 2001).
Birnie et al.,"*Antimicrobial Evaluation of N-Alkyl Betaines and N-Alkyl-N,N-Dimethylamine Oxides with Variations in Chain Length*", Antimicrobial Agents and Chemotherapy, 44 (9), pp. 2514-2517 (Sep. 2000).
Birnie et al., "*Antimicrobial and Diffusional Correlation of N-Alkyl Betaines and N-Alkyl-N,N-Dimethylamine Oxides From Semisolids*", Journal of Pharmaceutical Sciences, 90 (9), pp. 1386-1394 (Sep. 2001).
Banin et al., "*Chelator-Induced Dispersal and Killing of Pseudomonas aeruginosa Cells in a Biofilm*", Applied and Environmental Microbiology, 72 (3), pp. 2064-2069 (Mar. 2006).
Steinberg et al., "*Testing a Degradable Topical Varnish of Cetylpyridinium Chloride in an Experimental Dental Biofilm Model*", Journal of Antimicrobial Chemotherapy, 48 (2), pp. 241-224 (Aug. 2001).

(56) References Cited

OTHER PUBLICATIONS

Harrington et al., "*Antimicrobial Activity of Gallium against Virulent Rhodococcus Equi In Vitro and In Vivo*", Journal of Veterinary Pharmacology and Therapeutics, 29 (2), pp. 121-127 (Apr. 2006).
Stojiljkovic et al., "*Non-Iron Metalloporphyrins: Potent Antibacterial Compounds That Exploit haem/Hb Uptake Systems of Pathogenic Bacteria*", Molecular Microbiology, 31 (2), pp. 429-442 (Jan. 1999).
"Traditional Amine Oxides" BU ICS, Industrial & Home Care, Clariant, Inc. newsletter, Issue 8, pp. 1-7 (Aug. 2010).
Corner, A.M. et al., "C31G, a New Agent for Oral Use with Potent Antimicrobial and Antiadherence Properties", Antimicrobial Agents and Chemotherapy, vol. 32, No. 3, pp. 350-353 (Mar. 1988).
Datsenko B.M., Theory and practice of topical treatment of chronic festering wounds (Problems of therapy using medications), 2 pages (1995).

* cited by examiner

METHOD FOR TREATING CHRONIC WOUNDS WITH AN EXTRACELLULAR POLYMERIC SUBSTANCE SOLVATING SYSTEM

CROSS-REFERENCE TO RELATED APPLICATIONS

This application is a divisional of U.S. application Ser. No. 13/124,380 filed Apr. 14, 2011, entitled METHOD FOR TREATING CHRONIC WOUNDS WITH AN EXTRACELLULAR POLYMERIC SUBSTANCE SOLVATING SYSTEM (as amended), which in turn claims the benefit of International Application No. PCT/US2009/047101 filed Jun. 11, 2009, which in turn claims the benefit of U.S. Provisional Application Ser. No. 61/061,058 filed Jun. 12, 2008, both entitled METHOD FOR TREATING CHRONIC WOUNDS, the entire disclosures of each of which are incorporated herein by reference.

BACKGROUND

Chronic wounds affect millions of people, and are responsible for significant hospitalization costs and other expenses and inconvenience. Diabetics and people with other circulation impairments are susceptible to diabetic ulcers and venous stasis ulcers. Paralyzed, unconscious or severely debilitated patients are susceptible to decubitus ulcers. Although a variety of chronic wound care treatment therapies have been explored, many wounds can not be adequately treated. In some cases amputation of an affected limb may be the only available remedy.

SUMMARY OF THE INVENTION

We have found that chronic wounds may be treated by debriding at least some necrotic or other devitalized tissue from the wound, and applying to healthy or healable tissue in the wound an extracellular polymeric substance (EPS) solvating system comprising a metal ion sequestering agent, surfactant and buffering agent. The debriding and application steps desirably are combined by applying the solvating system using a sufficient flow rate or sufficient pressure to debride at least some devitalized tissue from the wound.

The invention provides in another aspect a method for treating a chronic wound, which method comprises applying to healthy or healable tissue in the wound an EPS solvating system comprising a metal ion sequestering agent, surfactant and buffering agent and having a an osmolarity of about 1,000 to about 4,000 milliosmoles (mOsm).

The invention provides in another aspect an apparatus for treating a chronic wound, comprising a debriding device; a reservoir containing an EPS solvating system comprising a metal ion sequestering agent, surfactant and buffering agent, in fluid communication with an applicator for applying the solvating system to a wound; and an aspirating device which removes at least some debrided necrotic or other devitalized tissue and excess solvating system from the wound. The solvating system applicator desirably also serves as the debriding device by applying the solvating system at a sufficient flow rate or under sufficient pressure to debride at least some devitalized tissue from the wound.

The invention provides in another aspect a patient care kit for treating a chronic wound, the kit comprising a tray; syringe; vessel containing an EPS solvating system comprising a metal ion sequestering agent, surfactant and buffering agent; and printed instructions describing the proper use of the kit for treating chronic wounds.

BRIEF DESCRIPTION OF THE DRAWING

Like reference symbols in the various figures of the drawing indicate like elements. The elements in the drawing are not to scale.

DETAILED DESCRIPTION OF THE PREFERRED EMBODIMENTS

The following detailed description describes certain embodiments and is not to be taken in a limiting sense. All weights, amounts and ratios herein are by weight, unless otherwise specifically noted. The terms shown below have the following meanings:

The phrase "antimicrobial agent" refers to a substance having the ability to cause greater than a 90% numeric reduction (viz., at least a 1-log order reduction) in a population of one or more aerobic or anaerobic bacteria present in chronic wounds.

The terms "attached" and "adhered" when used in reference to a bacterial biofilm and a surface mean that the biofilm is established on and at least partially coats or covers the surface, and has some resistance to removal from the surface. As the nature of this relationship is complex and poorly understood, no particular mechanism of attachment or adherence is intended by such usage.

The phrase "bacterial biofilm" means a community of bacteria attached to a surface, with the organisms in the community being contained within an EPS matrix produced by the bacteria.

The term "biocompatible" when used in reference to a substance means that the substance presents no significant deleterious or untoward effects upon the body.

The phrase "chronic wound" means a wound containing exposed devitalized or otherwise compromised tissue which will not heal in a medically acceptable time frame (e.g., within one or two months) through normal healing processes.

The term "debride" when used in reference to devitalized tissue attached within a chronic wound means to cut away or otherwise excise the tissue so that it is no longer attached. No particular mechanism of debridement is intended by such usage.

The terms "detaching", "removing" and "disrupting" when used in reference to a bacterial biofilm attached or adhered to a surface mean that at least a significant amount of the biofilm initially present on the surface no longer is attached or adhered to the surface. No particular mechanism of detachment, removal or disruption is intended by such usage.

The term "devitalized" when used in reference to wound tissue means tissue that is sufficiently devoid of life so that it will not heal if left untreated.

The term "osmolality" means the number of osmoles of solute per kilogram of solvent, as measured using a Model 5002 Osmette A™ freezing point depression osmometer (Precision Systems, Inc.).

The term "osmolarity" means the number of osmoles of solute per liter of solution. Osmolarity may conveniently be calculated from an osmolality measurement.

The phrase "sequestering agent" means a chemical that will combine with another material, especially a metal ion, to discourage or prevent the material from coming out of solution. The phrase "metal ion sequestering agent" means a sequestering agent that will combine with one or more metal ions such as alkali metals (viz., lithium, sodium, potassium, rubidium, cesium or francium), alkaline earth metals (viz., beryllium, magnesium, calcium, strontium, barium or radium), iron and the like to discourage or prevent the metal ion from coming out of solution.

The term "solvating" means to form a solution or dispersion containing a solvent or other carrier within which a solute is dissolved or suspended.

The term "wound" means an opening in the skin through which subdermal or deeper tissue (e.g., subcutaneous fat, muscle or other tissue) is exposed.

Figure 1:
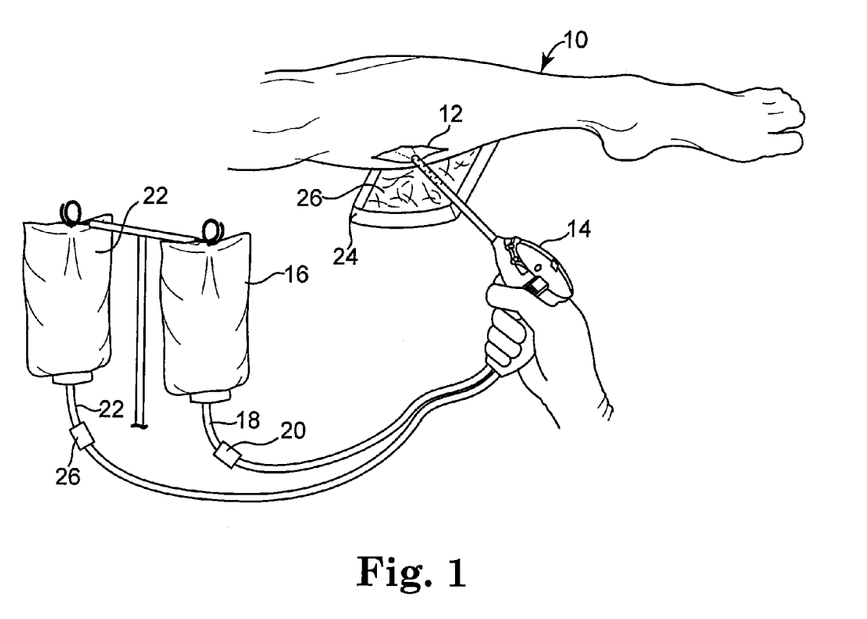
FIG. 1 is a perspective view of a chronic leg wound being treated with the disclosed solvating system.

Referring to FIG. 1, a leg 10 with chronic wound 12 (in this instance, a venous stasis ulcer) may be treated using a hydrodebriding device 14 which applies the disclosed EPS solvating system to wound 12 at a sufficient flow rate or under sufficient pressure to debride devitalized tissue. A variety of devices may be used or adapted as need be to provide device 14, including the Pulsavac™ and Pulsavac Plus™ wound debridement systems (Zimmer, Inc.), the SonicOne™ ultrasonic wound debridement system (Misonix, Inc.), the Versajet™ hydrosurgery system (Smith & Nephew, Inc.), the SpineJet™ hydrosurgery system (HydroCision, Inc.) and the MHS™ hydrodebriding system (Medtronic Xomed, Inc.). Device 14 may include or be connected to a suitable power source (e.g., a rechargeable battery or low voltage transformer) to operate a pump (not shown in FIG. 1) within device 14. The solvating system may be applied from a reservoir such as bag 16 in fluid communication via conduit 18 and valve 20 with device 14. Sterile saline or other suitable rinsing solution may if desired be supplied from a reservoir such as bag 22 in fluid communication via conduit 24 and valve 26 with device 14. If desired, other debridement techniques may be employed together with device 14, including cutting or scraping away devitalized tissue using a scalpel, scissors, swab, plastic stick, tongue depressor or other suitable tool such as the Straightshot™ M4 microdebrider (Medtronic Xomed, Inc.). The debrided devitalized tissue, wound exudates, excess solvating system solution, excess saline or other rinsing solution (if used) and other solid or fluid residues may be collected in pan 24. Absorbent pad 26 made from a nonwoven or other suitable material may help retain at least the fluid residues in pan 24. At the conclusion of treatment, a wound dressing (not shown in FIG. 1) may if desired be applied to wound 12 to discourage further infection.

Figure 2:
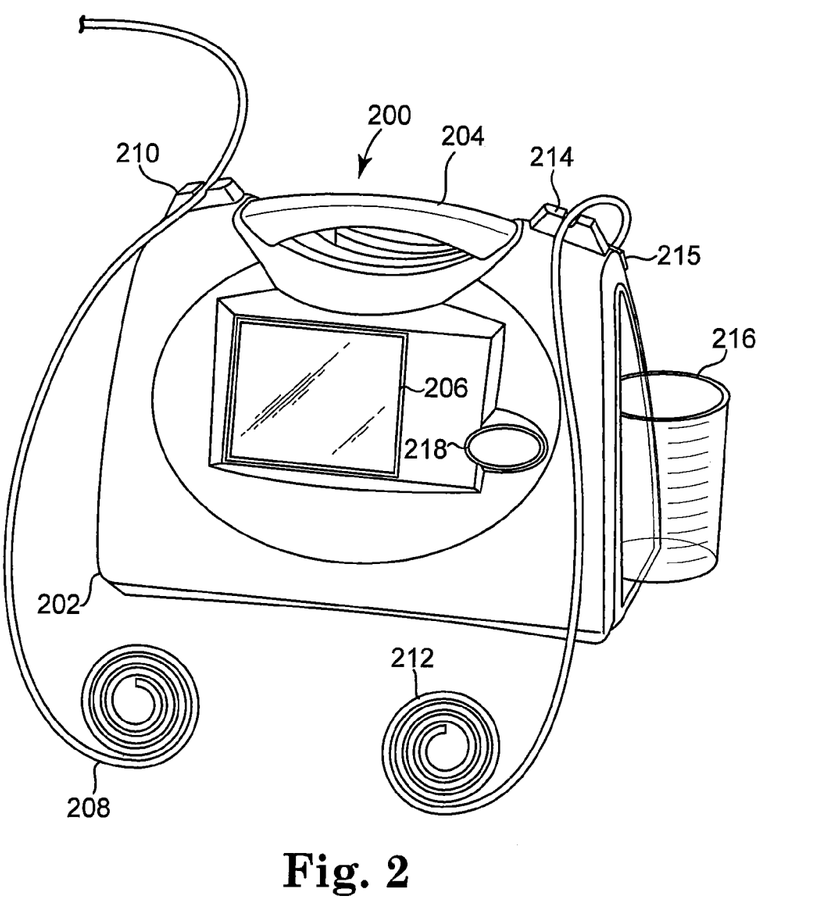
FIG. 2 is a perspective view of an apparatus for treating chronic wounds.

FIG. 2 shows a perspective view of another apparatus 200 for use in the disclosed method. A variety of devices may be used or adapted as need be to provide apparatus 200, including the V.A.C. Instill™ wound healing system from KCI Licensing (San Antonio, Tex., and the Invia™ healing system or the Dominant™ 35c/I suction system (both from Medela Healthcare U.S.). Apparatus 200 includes a housing 202 with handle 204. Touch screen display 206 may be used to control the operation of apparatus 200. The disclosed solvating system may be supplied from a bag or other suitable reservoir (for example, a bag like bag 16 in FIG. 1) to a chronic wound via tubing 208. The coiled end of tubing 208 may be connected to a suitable dispensing tip (not shown in FIG. 2) through which the disclosed solvating system may be delivered into a wound. Shoulder clamp 210 may be used to hold tubing 208 on apparatus 200. Debrided devitalized tissue, wound exudates, excess solvating system solution, excess saline or other rinsing solution (if used) and other solid or fluid residues may be collected from the wound using a suitable aspirating tip (not shown in FIG. 2) connected to the coiled end of tubing 212. The other end of tubing 212 is attached to a fitting 215 on housing 202 through which the collected solid or fluid residues pass into a pump (not shown in FIG. 2) inside housing 202. Shoulder clamp 214 may be used to hold tubing 212 on apparatus 200. A removable canister 216 may be used to collect and later dispose of solid and fluid residues passing through the pump. Release button 218 and an associated clamp or other retaining mechanism (not shown in FIG. 2) may be used to lock canister 216 in apparatus 200 until such time as removal of canister 216 is desired.

The apparatus shown in FIG. 2 does not itself deliver the disclosed solvating system to the wound. Debridement of devitalized tissue could be carried out using any convenient debridement technique including the cutting or scraping techniques mentioned above, or by excising the devitalized tissue using a separately-supplied directed fluid stream such as a pressurized sterile saline stream. The FIG. 2 apparatus may if desired be altered to permit pressurized delivery of solvating system solution, for example by adding a suitable separate pump, or by modifying the existing pump or associated tubing in apparatus 200 so that sufficient flow rate or sufficient pressure for hydrodebriding and sufficient suction for removal of solid and fluid residues from wounds are available in apparatus 200. The FIG. 2 apparatus may also be modified to provide additional measures for discouraging bacterial survival, regrowth or recolonization in the wound, including exposure of the wound to light (e.g., ultraviolet and other wavelengths of light, delivered as non-coherent or as laser radiation), sonication (e.g., ultrasound), gases (e.g., nitrogen or oxygen), heating, cooling, or agents which consume, complex, bind to or replace bacteria or bacterial nutrients such as iron or sugars.

Figure 3:
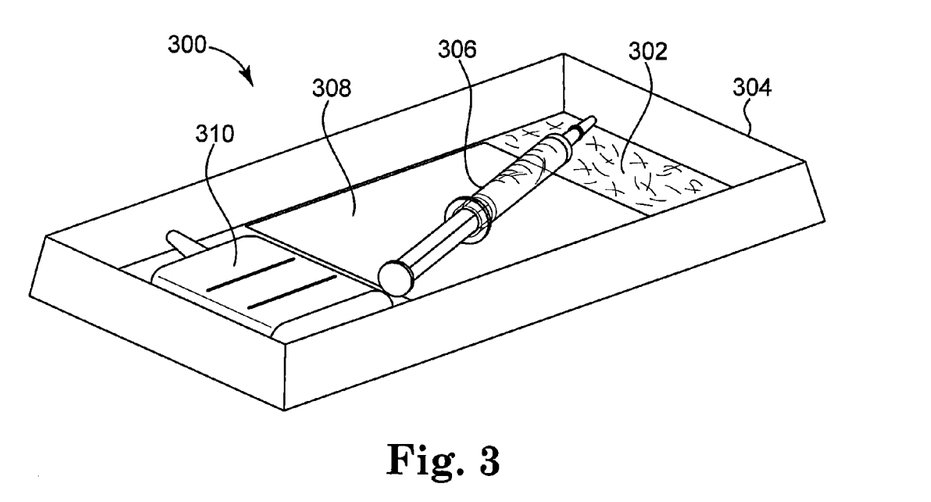
FIG. 3 is a perspective view of a home care kit for treating chronic wounds.

FIG. 3 shows a perspective view of a patient care kit 300 (e.g., a home care kit or travel kit) which may be employed in the disclosed method. Kit 300 includes tray 302 which may be lined with absorbent pad 304. Tray 302 may also contain or otherwise be packaged with syringe 306, printed instructions 308 describing the proper use of kit 300 in the home treatment of chronic wounds, and bottle 310 or other suitable vessel containing the disclosed solvating system. Kit 300 may also include one or more manual debriding tools (not shown in FIG. 3) such as a scissors, knife or swab and one or more wound dressings (also not shown in FIG. 3) for application to the wound following treatment. Syringe 306 may for example have a capacity of about 50 to about 75 cc (e.g., about 60 cc), and bottle 310 may for example have a capacity of about 2 to 5 times the capacity of syringe 306. Kit 300 may be sold over-the-counter or by prescription, with prescription sale being preferred in cases where further wound monitoring by a health care professional may be needed once kit 300 and any permitted solvating system refills have been consumed.

Chronic wounds treatable using the disclosed method wound typically will contain large colonies of one or more aerobic or anaerobic organisms occupying one or more biofilms. For long-term chronic wounds, more anaerobes than aerobes may be present. Representative organisms which may be present in chronic wound biofilms include *Staphylococcus* species (e.g., normal skin flora including *S. epidermidis, S. Corynebacterium* and *S. Brevibacterium*, and typical pathogens including *S. aureus*), other normal skin flora including *Proprionibacterium acnes*, and other pathogens, for example *Acinetobacter* species including *A. baumannii*, *Bacillus* species including *B. anthracis*, *Brucella* species including *B. melitensis*, *Clostridium* species including *C. tetani*, *Corynebacterium* species including *C. diphtheriae*, *Erysipelothrix* species including *E. rhusiopathiae*, *Escherichia* species including *E. coli*, *Klebsiella* species including *K. pneumoniae* or *K. oxytoca*, *Leptospira* species including *L. interrogans*, *Mycobacteria* species including *M. marinum* or *M. ulcerans*, *Proteus* species including *P. mirabilis*, *P. vulgaris* or *P. penneri*, *Pseudomonas* species including *P. aeruginosa* or *P. maltophilia*, *Stenotrophomonas* species including *S. maltophilila*, Beta-hemolytic *Streptococcus* species including *S. pyogenes* or *S. agalactiae*, *Treponema* species including *T. pallidum*, and *Yersinia* species including *Y. pestis*.

The wound may exhibit festering or other exudate production, swelling, erythema, pain, localized increased temperature, periwound cellulitis, ascending infection or a change in the appearance of granulation tissue (for example, discoloration, bleeding or friability). The wound may have been caused or aggravated due to a variety of external factors including abrasion, burns, compression, immersion, surgery or trauma. Frequently however the wound may be caused or aggravated and may remain chronic due to a variety of internal factors including a compromised circulatory system (e.g., as in many diabetic patients), a compromised immune system or diseases including impetigo, folliculitis, erysipelas, cellulitis or necrotizing fasciitis. Chronic foot or leg wounds in diabetic patients frequently involve colonies of *S. aureus* and Beta-hemolytic *Streptococcus*, are especially difficult to heal, and are of particular interest for treatment using the disclosed method since doing so may avoid amputation. The wound may be present in other body parts or in other extremities, and may be present not only in humans (including adults, children and the elderly) but also in animals (including livestock, pets, show animals and wild animals).

The disclosed solvating system may be used to break down bacterial biofilms in chronic wounds and consequently aid in biofilm detachment, removal or disruption. The solvating system preferably is biocompatible with healthy and healable wound tissues, and desirably does not contain ingredients which might potentially harm such tissues or unduly compromise wound healing. The solvating system desirably has a sufficiently low viscosity to enable easy delivery to the wound using for example power spray or other spray application, lavage, misting, mopping, wicking or dripping. The solvating system desirably also may be easily removed from the treatment site by subsequent aspiration, flushing, rinsing, draining or absorption (e.g., using an absorbent pad or other suitable material). While not wishing to be bound by theory, the metal ion sequestering agent may complex, bind or otherwise tie up metal ions which may crosslink, bridge or otherwise assist in binding together the polymer chains in an EPS matrix. The solvating agent may then surround the unbound polymer chains or fragments, breaking down the matrix, solvating the unbound polymer chains or fragments, and bringing them into solution or suspension where they can be easily flushed or otherwise removed from the wound site using for example additional amounts of the solvating system or a separate rinsing agent.

Solvating systems for use in certain tissue treatments are described in U.S. Patent Application Publication No. US 2007/0264296 A1 and PCT Published Application No. WO 2007/134055 A1. The solvating systems described in these publications have particular utility in ear, nose and throat applications such as the treatment of otitis media, cholesteatoma and rhinosinusitis. In general, these solvating systems have insufficient osmolarity for the efficacious treatment of chronic wounds, but they may be adapted for use in treating chronic wounds. Ciliated tissue such as that found in the ear, nose and throat is somewhat fragile, and to avoid damaging the cilia it is desirable to use solvating systems with low osmolarity, e.g., osmolarity of about 300 to about 900 mOsm. When treating chronic wounds, it is preferable to use a substantially higher osmolarity EPS solvating system, for example one whose osmolarity is about 1,000 to about 4,000 mOsm, more preferably about 1,500 to about 2,600 mOsm. Doing so may facilitate wound treatment or wound healing.

The metal ion sequestering agent desirably is a mild acid whose acidity is sufficient to sequester one or more metal ions in the EPS matrix, but which is not so acidic so as to harm healthy or healable wound tissue. Metal ions of particular interest (due to their likely involvement in the targeted bacterial biofilms) include sodium, calcium and iron. The metal ion sequestering agent desirably is water-soluble and not unduly toxic. Representative acids include but are not limited to carboxylic acids, diacids, or triacids such as formic acid, acetic acid, chloroacetic acid, dichloroacetic acid, oxalic acid, oxamic acid, glycolic acid, lactic acid, pyruvic acid, aspartic acid, fumaric acid, maleic acid, succinic acid, iminodiacetic acid, glutaric acid, 2-ketoglutaric acid, glutamic acid, adipic acid, citric acid, glucuronic acid, mucic acid, nitrilotriacetic acid, salicylic acid, ketopimelic acid, benzoic acid, mandelic acid, chloromandelic acid, phenylacetic acid, phthalic acid and boric acid; mineral acids such as hydrochloric acid, orthophosphoric acid and phosphonic acid; and mixtures thereof. Citric acid is a preferred acid. The metal ion sequestering agent may for example be present at a concentration of at least about 0.01 M, at least about 0.05 M or at least about 0.1 M, e.g., about 0.01 to about 1.5 M. Increased metal ion sequestering agent amounts may promote faster biofilm breakup.

The solvating system also includes a surfactant. The surfactant desirably is water-soluble and nontoxic. Exemplary surfactants include anionic surfactants, nonionic surfactants, cationic surfactants and zwitterionic surfactants. Exemplary anionic surfactants include but are not limited to $C_6$-$C_{24}$ alkylbenzene sulfonates; $C_6$-$C_{24}$ olefin sulfonates; $C_6$-$C_{24}$ paraffin sulfonates; cumene sulfonate; xylene sulfonate; $C_6$-$C_{24}$ alkyl naphthalene sulfonates; $C_6$-$C_{24}$ alkyl or dialkyl diphenyl ether sulfonates or disulfonates, $C_4$-$C_{24}$ mono or dialkyl sulfosuccinates; sulfonated or sulfated fatty acids; $C_6$-$C_{24}$ alcohol sulfates (for example $C_6$-$C_{12}$ alcohol sulfates); $C_6$-$C_{24}$ alcohol ether sulfates having 1 to about 20 ethylene oxide groups; $C_4$-$C_{24}$ alkyl, aryl or alkaryl phosphate esters or their alkoxylated analogues having 1 to about 40 ethylene, propylene or butylene oxide units; and mixtures thereof. For example, the anionic surfactant may be sodium chenodeoxycholate, N-lauroylsarcosine sodium salt, lithium dodecyl sulfate, 1-octanesulfonic acid sodium salt, sodium cholate hydrate, sodium deoxycholate, sodium dodecyl sulfate (also known as sodium lauryl sulfate) or sodium glycodeoxycholate.

Exemplary cationic surfactants include but are not limited to quaternary amine compounds having the formula:

where R, R', R" and R'" are each a $C_1$-$C_{24}$ alkyl, aryl or aralkyl group that can optionally contain one or more P, O, S or N heteroatoms, and X is F, Cl, Br, I or an alkyl sulfate. For example, the cationic surfactant may be hexadecylpyridinium chloride monohydrate or hexadecyltrimethylammonium bromide.

Exemplary nonionic surfactants include but are not limited to $C_6$-$C_{24}$ alcohol ethoxylates (for example $C_6$-$C_{14}$ alcohol ethoxylates) having 1 to about 20 ethylene oxide groups (for example about 9 to about 20 ethylene oxide groups); $C_6$-$C_{24}$ alkylphenol ethoxylates (for example $C_8$-$C_{10}$ alkylphenol ethoxylates) having 1 to about 100 ethylene oxide groups (for example about 12 to about 20 ethylene oxide groups); $C_6$-$C_{24}$ alkylpolyglycosides (for example $C_6$-$C_{20}$ alkylpolyglycosides) having 1 to about 20 glycoside groups (for example about 9 to about 20 glycoside groups); $C_6$-$C_{24}$ fatty acid ester ethoxylates, propoxylates or glycerides; $C4$-$C_{24}$ mono or di alkanolamides; and mixtures thereof. For example, the nonionic surfactant may be polyoxyethyleneglycol dodecyl ether, N-decanoyl-N-methylglucamine, digitonin, n-dodecyl B-D-maltoside, octyl B-D-glucopyranoside, octylphenol ethoxylate, polyoxyethylene (8) isooctyl phenyl ether, polyoxyethylene sorbitan monolaurate or polyoxyethylene (20) sorbitan monooleate.

Exemplary zwitterionic surfactants include but are not limited to aminoalkylsulfonate compounds having the formula:

where R, R', R" and R'" are each a $C_1$-$C_{24}$ alkyl, aryl or aralkyl group that can optionally contain one or more P, O, S or N heteroatoms; amine oxide compounds having the formula:

where R, R' and R" are each a $C_1$-$C_{24}$ alkyl, aryl or aralkyl group that can optionally contain one or more P, O, S or N heteroatoms; and betaine compounds having the formula:

where R, R' and R" are each a $C_1$-$C_{24}$ alkyl, aryl or aralkyl group that can optionally contain one or more P, O, S or N heteroatoms, and n is about 1 to about 10. For example, the zwitterionic surfactant may be 3-[(3-cholamidopropyl) dimethylammonio]-2-hydroxy-1-propane sulfonate, 3-[(3-cholamidopropyl) dimethylammonio]-1-propane sulfonate (sometimes referred to as CHAPS), 3-(decyldimethylammonio) propanesulfonate inner salt (sometimes referred to as caprylyl sulfobetaine), or N-dodecyl-N,N-dimethyl-3-ammonio-1-propanesulfonate.

Preferred surfactants include alkyl sulfates, alkyl sulfonates, aryl sulfonates and zwitterionic surfactants. The desired surfactants may be obtained as pure compounds or in some instances may be obtained by using products such as liquid Castile soap. The surfactant may for example be present at a concentration of at least about 0.002 M, at least about 0.005 M or at least about 0.01 M, e.g., about 0.002 to about 1 M, about 0.005 to about 0.7 M or about 0.01 to about 0.5 M. Expressed on a weight basis, the surfactant preferably is greater than 0.2 wt. % of the solvating system and may for example be about 0.3% to about 30%, about 0.5% to about 25% or about 1% to about 20% of the solvating system. Increased surfactant amounts may promote faster biofilm breakup.

The solvating system also includes a buffering agent. The buffering agent preferably maintains the solvating system at an appropriate pH for contacting the wound, e.g., at a pH greater than about 4 or greater than about 5. For example, the solvating system may be buffered to have a near-neutral pH, e.g., a pH greater than about 5 and less than about 8.5. Buffering agents may for example be up to about 50% of the solvating system. Exemplary buffering agents include but are not limited to potassium chloride, glycine, potassium hydrogen phthalate, sodium acetate, potassium hydrogen phthalate, barbitone sodium and sodium citrate. When the metal ion sequestering agent is a mild acid, the buffering agent desirably is a salt of that acid.

The solvating system also includes water. The water may be distilled, deionized or sterile water. Water may for example be at least 50%, at least 60% or at least 75% of the solvating system.

The solvating system may optionally include various other ingredients, including nonaqueous solvents (e.g., alcohols), antimicrobial agents, therapeutic agents and a variety of adjuvants. Solvating systems which do not contain antimicrobial agents may be preferred for some applications, for example where there may be a risk that an antimicrobial agent might promote the evolution of more resistant bacteria. Solvating systems containing one or more antimicrobial agents, and especially one or more topical antibiotic agents (viz., antibiotics which may be applied to the skin and which in connection with the disclosed method are applied in a chronic wound), may be preferred for other applications. The EPS matrix may allow a biofilm to stick to an underlying tissue surface while protecting the embedded organisms. The bacteria in such a biofilm may be approximately 100 to 1000 times more resistant to the effects of antibiotics than planktonic bacteria. After the biofilm has been broken down into unbound polymers or fragments and solvated or otherwise disrupted by the solvating system, an antimicrobial agent can much more effectively attack the remaining bacteria. Exemplary antimicrobial agents include active oxygen compounds such as hydrogen peroxide, isolated or equilibrium derived or isolated peracids such as chloroperbenzoic acids, peracetic acid, perheptanoic acid, peroctanoic acid, perdecanoic acid, performic acid, percitric acid, perglycolic acid, perlactic acid, perbenzoic acid, and monoester peracids derived from diacids or diesters such as adipic, succinic, glutaric, or malonic acid; amphenicols; ampicillins; ansamycins; beta-lactams such as carbacephems, carbapenems, cephalosporins, cephamycins, monobactams, oxacephems, penicillins and any of their derivatives; carboxylic esters such as p-hydroxy alkyl benzoates and alkyl cinnamates; chitosan salts; cubic-phase lipids; gallium-containing antimicrobial agents such as gallium acetylacetonate, gallium bromide, gallium chloride, gallium fluoride, gallium iodide, gallium maltolate, gallium nitrate, gallium nitride, gallium percolate, gallium phosphide and gallium sulfate; iodo-compounds and other active halogen compounds such as iodine, interhalides, polyhalides, metal hypochlorites, hypochlorous acid, metal hypobromites, hypobromous acid, chloro- and bromo-hydantoins, chlorine dioxide and sodium chlorite; lincosamides; macrolides; nitrofurans; organic peroxides including benzoyl peroxide and alkyl benzoyl peroxides; ozone; phenolic derivatives including o-phenyl phenol, o-benzyl-p-chlorophenol, tert-amyl phenol and $C_1$-$C_6$ alkyl hydroxy benzoates; quaternary ammonium compounds such as alkyldimethylbenzyl ammonium chloride and dialkyldimethyl ammonium chloride; quinolines; singlet oxygen generators; sulfonamides; sulfones; sulfonic acids such as dodecylbenzene sulfonic acid; tetracyclines; vancomycin; derivatives thereof and mixtures thereof. Many of these recited agents represent classes containing useful specific materials whose individual utility will be recognized by persons having ordinary skill in the art. For example, exemplary penicillins include but are not limited to amdinocillin, amdinocillin pivoxil, amoxicillin ampicillin, apalcillin, aspoxicillin, axidocillin, azlocillin, acampicillin, bacampicillin, benzylpenicillinic acid, benzylpenicillin sodium, carbenicillin, carindacillin, clometocillin, cloxacillin, cyclacillin, dicloxacillin, epicillin, fenbenicillin, floxacillin, hetacillin, lenampicillin, metampicillin, methicillin sodium, mezlocillin, nafcillin sodium, oxacillin, penamecillin, penethamate hydriodide, penicillin G benethamine, penicillin G benzathine, penicillin G benzhydrylamine, penicillin G calcium, penicillin G hydrabamine, penicillin G potassium, penicillin G. procaine, penicillin N, penicillin O, penicillin V, penicillin V banzathine, penicillin V hydrabamine, penimepicycline, phenethicillin potassium, piperacillin, pivampicillin propicillin, quinacillin, sulbenicillin, sultamicillin, talampicillin, temocillin, ticarcillin and mixtures thereof or with other materials (e.g., penicillins combined with clavulanic aid such as the combination of amoxicillin and clavulanic acid available as Augmentin™ from GlaxoSmithKline).

Preferably the antimicrobial agent provides greater than a 99% numeric reduction (viz., at least a 2-log order reduction), greater than a 99.9% numeric reduction (viz., at least a 3-log order reduction), greater than a 99.99% numeric reduction (viz., at least a 4-log order reduction) or greater than a 99.999% numeric reduction (viz., at least a 5-log order reduction) in a population of one or more aerobic or anaerobic bacteria present in chronic wounds.

Exemplary therapeutic agents include any material suitable for use in wound treatment including analgesics, anticholinergics, anti-fungal agents, steroidal or non-steroidal anti-inflammatory agents, anti-parasitic agents, antiviral agents, biostatic compositions, chemotherapeutic/antineoplastic agents, cytokines, immunosuppressors, nucleic acids, peptides, proteins, steroids, vasoconstrictors, vitamins, mixtures thereof, and other therapeutic materials. Bacterially selective peptides may, for example, provide a more useful or safer therapeutic effect against some pathogens than that provided by broad spectrum antibiotics.

Adjuvants which may be included in the solvating system include dyes, pigments or other colorants (e.g., FD & C Red No. 3, FD & C Red No. 20, FD & C Yellow No. 6, FD & C Blue No. 2, D & C Green No. 5, D & C Orange No. 4, D & C Red No. 8, caramel, titanium dioxide, fruit or vegetable colorants such as beet powder or beta-carotene, turmeric, paprika and other materials that will be familiar to those skilled in the art); indicators; antioxidants; antifoam agents; and rheology modifiers including thickeners and thixotropes.

The wound may be debrided to detach devitalized tissue using manual debriding tools such as those described above. Preferably the wound is debrided using a directed stream of the disclosed solvating system or other suitable fluid. The flow rate or pressure desirably are high enough to promote rapid and sufficiently complete debriding, and low enough to avoid undue pain or injury to healthy or healable wound tissue. At least part and preferably all of the devitalized wound tissue is debrided.

The solvating system desirably is applied to at least an extent sufficient to cover healthy or healable tissue in the wound. In some instances it will be desirable to apply the solvating system within and not merely atop exposed tissue within the wound. Sufficient solvating system should be applied to the wound and to a targeted biofilm contained therein so that the biofilm and its organisms are wholly or partially disrupted, solvated or removed, either during treatment or at some subsequent time. Doing so may involve chemical dilution or mechanical disruption, and may be accompanied by breakdown of the biofilm EPS matrix through calcium ion sequestering by the metal ion sequestering agent, and by solvation of the resulting breakdown fragments (e.g., mannuronic and guluronic acids) into aqueous solution so as to facilitate their removal using aspiration, lavage or other removal techniques. High flow rates (for example, more than 7 and less than 20 $cm^3$/sec) or high delivery pressures (for example, about 30 to about 500 KPa or about 60 to about 350 KPa, as measured at the pump outlet when the desired application tip is attached) may assist in wound debridement and biofilm disruption. It may be desirable to apply sufficient solvating system into the wound to displace any pus or other wound exudates which may be present, allowing excess solvating system to overflow from the wound until the color of the excess solvating system no longer changes. The solvating system may be left in place until it can drain away or is otherwise eliminated or resorbed, or the solvating system may be allowed to stand for a suitable time (e.g., a few minutes, a few hours or longer) and then may be rinsed away using sterile saline or another suitable liquid. Application of the solvating system and removal of dislodged or disrupted biofilm and bacteria may also be repeated as desired for more thorough removal of the offending organisms.

The solvating system may desirably be used as a part of a multi-step treatment regimen which disrupts the bacterial biofilm and discourages its return. For example, a series of steps that may be broadly classified as Cleansing/Disrupting, Killing, Protecting/Coating, Aerating, and Healing may be carried out. The Cleansing/Disrupting step may be carried out by applying the solvating system to a chronic wound as described above. The Killing step may be carried out by applying a suitable antimicrobial agent to the wound site. This may for example be accomplished by including an antimicrobial agent in the solvating system or by separately applying such an agent intra operatively or post operatively (e.g., topically, orally or systemically). The Killing step may employ additional measures to discourage bacterial survival, regrowth or recolonization in the wound, e.g., as discussed above in connection with the FIG. 2 apparatus. The Protecting/Coating step may be carried out by coating at least part of the treated wound with a protective sealant layer. The sealant may provide a variety of benefits such as discouraging or preventing recolonization of the wound with bacteria and new biofilm-forming colonies; reducing inflammation; improving wound healing or allowing for the recovery of the body's natural innate immune response. The sealant may include one or more antimicrobial agents to further attack any bacterial biofilm, biofilm fragments or bacteria remaining following the Cleansing/Disrupting step described above, and to discourage its or their return. A preferred sealant may be based on the sealant disclosed in U.S. Patent Publication No. US 2007/0264310 A1, filed Apr. 24, 2007. The Aerating step may be carried out by applying a wound dressing with a suitable opening or openings (e.g., slits or pores) and leaving it or them open for a period of time sufficient to allow aeration of the treated wound. The Healing step may be carried out by allowing the cleansed, protected and optionally sealed wound to undergo a return to a normal state, e.g., through one or more normal healing mechanisms such as an inflammatory response, fibroblast proliferation and wound remodeling.

The invention is further described in the following Example, in which all parts and percentages are by weight unless otherwise indicated.

EXAMPLE

Biofilm Formation.

*Pseudomonas aeruginosa* PAO1 (ATCC number: BAA-47), *Enterococcus faecalis* V583 (ATCC number: 700802), and *Staphylococcus aureus* Mu50 (ATCC number: 700699) grown on agar plates made from tryptic soy broth (TSB, Sigma Chemical Co., St. Louis, Mo., USA) were inoculated into TSB broth and grown at 37° C. in a shaker for 16 hr. An aliquot was diluted in TSB broth to a series of dilutions for each individual bacteria type. The diluted bacteria were plated out to count colony forming units (CFU). They were further diluted to $1 \times 10^6$ cfu ml$^{-1}$ and mixed equally as inoculums. Bolton broth (Oxoid Ltd, Basingstock, Hampshire, England) with 50% Bovine plasma (Biomeda, Foster City, Calif., USA) was used for biofilm formation media. Glass 16×150 mm test tubes with caps were autoclaved, and 7 ml biofilm formation media aseptically dispensed in each tube. The normalized cultures of the three bacteria were mixed and 10 µl portions of the combined and normalized $1 \times 10^6$ CFU ml$^{-1}$ culture were inoculated into glass tubes by ejecting the pipette tips into the tubes. The pipette tip acts as a surface for biofilm formation. The tubes were then grown at 37° C. in a shaker for 24 hours at 140 rpm.

Solvating System Preparation.

A solvating system (referred to below as "CAZS") was prepared at three osmolarity levels by combining deionized water, caprylyl sulfobetaine zwitterionic surfactant ($CH_3(CH_2)_9N^+(CH_3)_2CH_2CH_2CH_2SO_3^-$, CAS 15163-36-7), citric acid (CAS 77-92-9) and sufficient sodium citrate (CAS 6132-04-3) to buffer the system to pH 5.5, using the amounts shown below in Table 1:

TABLE 1

| Ingredient | Osmolarity, mOsm | | |
|---|---|---|---|
| | 830 | 1,586 | 3,628 |
| Caprylyl Sulfobetaine (g/L) | 5.08 | 5.15 | 5.35 |
| Citric Acid (g/L) | 5.78 | 12.5 | 25 |
| Sodium Citrate (g/L) | 55.13 | 120.5 | 240.5 |
| pH | 5.5 | 5.5 | 5.5 |

Incubation with Formed Biofilms.

In a series of runs the formed biofilms were washed and then incubated with the three CAZS solutions, then associated with a 30 µg/ml solution of Gentamicin sulfate (MP Biomedicals, Illkirch, France) in distilled water, or with a 20 ppm solution of 2,4,4'-trichloro-2-hydroxydiphenyl ether (Triclosan, KIC Chemicals, New Paltz, N.Y., USA) dissolved in propylene glycol (ScienceLab, Houston, Tex., USA). The resulting mixtures were stirred at 37° C. and 140 rpm for 1, 2, 3 and 4 hours. Biofilm formation was subjectively observed and the biofilms were collected. A set of tubes with biofilms were placed in an oven at 80° C. for 48 hours to obtain a dry weight. The biomass dry weight was measured as the total weight minus the empty tube weight measured before use. Tests were performed in triplicate for each treatment group. A separate set of tubes in triplicate was used for DNA extraction and quantitative PCR analysis to determine relative bacterial levels in the treated biofilms. The results for the 830 and 1,586 mOsm CAZS solutions are shown below in Table 2:

TABLE 2

| Sample | Dry Weight, mg | Relative Bacterial Levels | | |
|---|---|---|---|---|
| | | P. aeruginosa | E. faecalis | S. aureus |
| Control | 126 | 46.8 | 29.7 | 23.5 |
| 20 mg/ml Gentamicin | 78 | 0.2 | 50.3 | 49.6 |
| 20 mg/ml Gentamicin + 200 µl 830 mOsm CAZS | 68.5 | 0.2 | 49.7 | 50.1 |
| 20 mg/ml Gentamicin + 200 µl 1,586 mOsm CAZS | 68 | 0.1 | 62.2 | 37.8 |
| 20 ppm Triclosan | 88 | 60.0 | 39.9 | 0.13 |
| 20 ppm Triclosan + 200 µl 830 mOsm CAZS | 28.5 | 53.0 | 47.0 | 0.1 |
| 20 ppm Triclosan + 200 µl 1,586 mOsm CAZS | 15 | 69.1 | 30.9 | 0.1 |
| 200 µl 830 mOsm CAZS | 115.5 | 45.0 | 32.7 | 22.4 |
| 200 µl 1,586 mOsm CAZS | 87 | 51.1 | 35.1 | 13.8 |

The results in Table 2 show that the biofilm dry weight was reduced using all treatments. Biofilm dry weight was also reduced using the CAZS solution alone, and further reduced when used in combination with Triclosan. CAZS solution also appeared to exhibit a selective inhibitory effect on *S. aureus*.

Although specific embodiments have been illustrated and described herein for purposes of description of the preferred embodiments, it will be appreciated by those of ordinary skill in the art that a wide variety of alternate or equivalent implementations calculated to achieve the same purposes may be substituted for the specific embodiments shown and described without departing from the scope of the present invention. This application is intended to cover any adaptations or variations of the preferred embodiments discussed herein. Therefore, it is manifestly intended that this invention be limited only by the claims and the equivalents thereof.

We claim:

1. An apparatus for treating a chronic wound, comprising:
   a) a debriding device comprising a reservoir containing an extracellular polymeric substance solvating system comprising an aqueous solution of a metal ion sequestering agent, surfactant and buffering agent wherein the solvating system has an osmolarity of about 1,000-4,000 milliosmoles of solute per liter, and wherein the reservoir is in fluid communication with an applicator for applying the solvating system to a wound at a sufficient flow rate or under sufficient pressure to debride at least some devitalized tissue from the wound; and b) an aspirating device which removes at least some debrided necrotic or other devitalized tissue and excess solvating system from the wound.

2. An apparatus according to claim 1 wherein the applicator applies the solvating system at a flow rate more than 7 and less than 20 cm$^3$/sec.

3. An apparatus according to claim 1 wherein the applicator applies the solvating system at a delivery pressure of about 30 to about 500 KPa.

4. An apparatus according to claim 1 wherein the applicator applies the solvating system at a delivery pressure of about 60 to about 350 KPa.

5. An apparatus according to claim 1 wherein the metal ion sequestering agent comprises a mild acid whose acidity is sufficient to sequester one or more metal ions in a bacterial biofilm but which is not so acidic so as to harm healthy or healable tissue in the wound.

6. An apparatus according to claim 1 wherein the metal ion sequestering agent comprises a sequestering agent for sodium, calcium or iron.

7. An apparatus according to claim 1 wherein the metal ion sequestering agent comprises a carboxylic acid, diacid, triacid or mixture thereof.

8. An apparatus according to claim 1 wherein the metal ion sequestering agent comprises formic acid, acetic acid, chloroacetic acid, dichloroacetic acid, oxalic acid, oxamic acid, glycolic acid, lactic acid, pyruvic acid, aspartic acid, fumaric acid, maleic acid, succinic acid, iminodiacetic acid, glutaric acid, 2-ketoglutaric acid, glutamic acid, adipic acid, glucuronic acid, mucic acid, nitrilotriacetic acid, salicylic acid, ketopimelic acid, benzoic acid, mandelic acid, chloromandelic acid, phenylacetic acid, phthalic acid, boric acid or mixture thereof.

9. An apparatus according to claim 1 wherein the metal ion sequestering agent comprises citric acid.

10. An apparatus according to claim 1 wherein the surfactant comprises an alkyl sulfate, alkyl sulfonate or aryl sulfonate or mixture thereof.

11. An apparatus according to claim 1 wherein the solvating system comprises at least about 0.01 M of metal ion sequestering agent and at least about 0.002 M of surfactant.

12. An apparatus according to claim 1 wherein the buffering agent maintains the solvating system at an appropriate pH for contacting chronic skin wounds.

13. An apparatus according to claim 1 wherein the solvating system has an osmolarity of about 1,500 to about 2,600 milliosmoles of solute per liter.

14. An apparatus according to claim 1 wherein the solvating system breaks down bacterial biofilms in chronic wounds.

15. An apparatus according to claim 1 wherein the solvating system aids in chronic wound biofilm detachment, removal or disruption.

16. An apparatus according to claim 1 wherein the solvating system further comprises an antimicrobial agent.

17. An apparatus according to claim 16 wherein the antimicrobial agent comprises a topical antibiotic.

18. An apparatus according to claim 16 wherein the antimicrobial agent comprises a peptide.

19. An apparatus according to claim 16 wherein the antimicrobial agent comprises a bacterially selective peptide.

20. An apparatus according to claim 16 wherein the antimicrobial agent comprises gallium acetoacetonate, gallium bromide, gallium chloride, gallium fluoride, gallium iodide, gallium maltolate, gallium nitrate, gallium nitride, gallium percolate, gallium phosphite, gallium sulfate or mixture thereof.

21. A patient care kit for treating a chronic wound, the kit comprising a tray; syringe; vessel containing an extracellular polymeric substance solvating system comprising an aqueous solution of a metal ion sequestering agent, surfactant and buffering agent wherein the solvating system has an osmolarity of about 1,000-4,000 milliosmoles of solute per liter; and printed instructions describing the proper use of the kit for treating chronic wounds.

22. A product comprising an extracellular polymeric substance solvating system for use in treatment of chronic skin wounds, the solvating system comprising an aqueous solution of at least about 0.01 M of metal ion sequestering agent, at least about 0.002 M of surfactant, and buffering agent that maintains the solvating system at an appropriate pH for contacting chronic skin wounds, wherein the solvating system has an osmolarity of about 1,000-4,000 milliosmoles of solute per liter, a sufficiently low viscosity to enable delivery to the wound using spray application, and aids in chronic wound biofilm detachment, removal or disruption.

* * * * *